(12) United States Patent
Vonderwalde et al.

(10) Patent No.: US 11,666,425 B2
(45) Date of Patent: Jun. 6, 2023

(54) DENTAL AEROSOL AND LIQUID SUCTION DEVICE

(71) Applicant: MAYCHER HEALTH CARE INNOVATIONS INC., Vancouver (CA)

(72) Inventors: Carlos Vonderwalde, Richmond (CA); David John Maycher, Vancouver (CA)

(73) Assignee: MAYCHER HEALTH CARE INNOVATIONS INC., Vancouver (CA)

( * ) Notice: Subject to any disclaimer, the term of this patent is extended or adjusted under 35 U.S.C. 154(b) by 263 days.

(21) Appl. No.: 16/944,523

(22) Filed: Jul. 31, 2020

(65) Prior Publication Data

US 2020/0360122 A1  Nov. 19, 2020

Related U.S. Application Data

(63) Continuation-in-part of application No. 15/328,142, filed on Jan. 23, 2017, now Pat. No. 10,765,497.

(60) Provisional application No. 62/028,078, filed on Jul. 23, 2014.

(51) Int. Cl.
*A61C 17/08* (2006.01)
*A61C 17/06* (2006.01)
*A61M 1/00* (2006.01)

(52) U.S. Cl.
CPC ............ *A61C 17/08* (2019.05); *A61C 17/096* (2019.05); *A61M 1/86* (2021.05)

(58) Field of Classification Search
CPC ..... A61C 17/043; A61C 17/041; A61C 17/04; A61C 17/06; A61C 17/096; A61C 17/10; A61C 17/08; A61C 19/01; A61M 1/008; A61M 1/86; A61M 25/02; A61M 2025/0253; A61M 2025/022; A61M 2025/0206

See application file for complete search history.

(56) References Cited

U.S. PATENT DOCUMENTS 3,049,806 A * 8/1962 Cofresi .................. A61C 17/08
433/93
4,865,545 A * 9/1989 La Rocca ............... A61C 17/08
433/96

* cited by examiner

*Primary Examiner* — Cris L. Rodriguez
*Assistant Examiner* — Drew S Folgmann
(74) *Attorney, Agent, or Firm* — Gowling WLG (Canada) LLP

(57) ABSTRACT

The present invention relates to dental suction devices for capturing aerosols and managing fluid accumulations in a patient's mouth during a dental procedure. The dental suction devices comprise a housing tube having a first end connectible to a vacuum source; a funnel demountably engageable with a second end of the housing tube; a pliable tube extending throughout the housing tube and extending outward from the funnel. The first end of the pliable tube is connectible to the vacuum source and its opposite end is positionable in a patient's mouth. The second end of the pliable tube has a plurality of apertures, and one or more pairs of retaining collars adjustably spaced-apart therealong. The pliable tube may be looped around the end of a row of teeth and secured in place by a tie that is secured to the spaced-apart pair of retaining collars between two adjacent teeth.

19 Claims, 18 Drawing Sheets

DENTAL AEROSOL AND LIQUID SUCTION DEVICE

FIELD OF THE INVENTION

The present invention relates to the field of suction devices and, in particular, to dental suction devices for capturing aerosols and managing fluid accumulations in a patient's mouth during dental procedures.

BACKGROUND OF THE INVENTION

Dental suction devices, also known as saliva ejectors, moisture evacuators, or suction hoses, may be used to vacuum saliva and debris from a patient's mouth in order to maintain a dry and clear operation space therein. Conventional dental suction devices typically comprise rigid or semi-rigid tubing that is periodically inserted into the patient's mouth by a dental professional during a procedure or, alternatively, that is hooked onto the side of the patient's mouth to enable hands-free operations. The insertion of such devices into the patient's mouth may be disruptive to the dental procedure, while hooking such devices to the side of the patient's mouth may be uncomfortable and cause tissue abrasions and bruising.

Another issue that may arise while performing dental procedures is the release of aerosols (i.e. fine solid particles or fine liquid droplets suspended in air) that may be harmful to the patient or the dental professional. For example, during ultrasonic cleanings or water sprayings, water-based aerosols that may carry viruses and/or bacteria may be created. Other sources of aerosols may include tooth polishing, filling removals (which, if the filling is old, may contain mercury), and filling replacements. The aerosols may then be unintentionally inhaled by the patient or the dental professional. Furthermore, these aerosols can be suspended in the air in the dental office for several hours posing a threat for next patients and the public in general.

High-volume evacuation systems (HVEs) may be used to capture aerosols produced during dental procedures. Some conventional HVEs are inserted into a patient's mouth by a dental professional. Such conventional HVEs must be within 1 cm to 1.5 cm of the aerosol source and therefore, must be frequently repositioned follow the aerosol-producing instrument around in the mouth. Other conventional HVEs are mounted externally at a distance away (for example, 6 inches to 10 inches) from the patient's mouth. In the same manner as discussed above, the insertion of the HVEs may be disruptive to the dental procedure. As well, positioning of an externally mounted HVE may have to be manually adjusted if the dentist or hygienist reposition the patient's head during the procedure, or if the patient moves, or if the hands of the dental professional obstruct the suction, thereby disrupting the dental procedure.

SUMMARY OF THE INVENTION

The embodiments of the present disclosure relate to dental suction devices for capturing aerosols and managing accumulations of fluid in a patient's mouth during a dental procedure.

According to one example of an embodiment of the present disclosure, there is disclosed a dental suction device comprising: a housing tube having a first end and a second end, the first end being connectible to a vacuum source; a funnel demountably engaged with the second end of the housing tube; a pliable tube extending throughout the housing tube and out from the funnel at the second end of the housing tube, the pliable tube having a first end connectable to the vacuum source and a second end for positioning in a patient's mouth, the second end having a plurality of apertures through which fluid may be suctioned from the patient's mouth; one or more pairs of retaining collars, wherein each pair of retaining collars comprises a first retaining collar securely positioned at a distance apart from a second retaining collar along the second end of the tube; and a tie connecting each pair of retaining collars so as to create a loop about the second end of the tube, wherein the loop is hookable around the terminal end of a row of teeth and each tie is securable between teeth in the row to secure the device in the patient's mouth.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
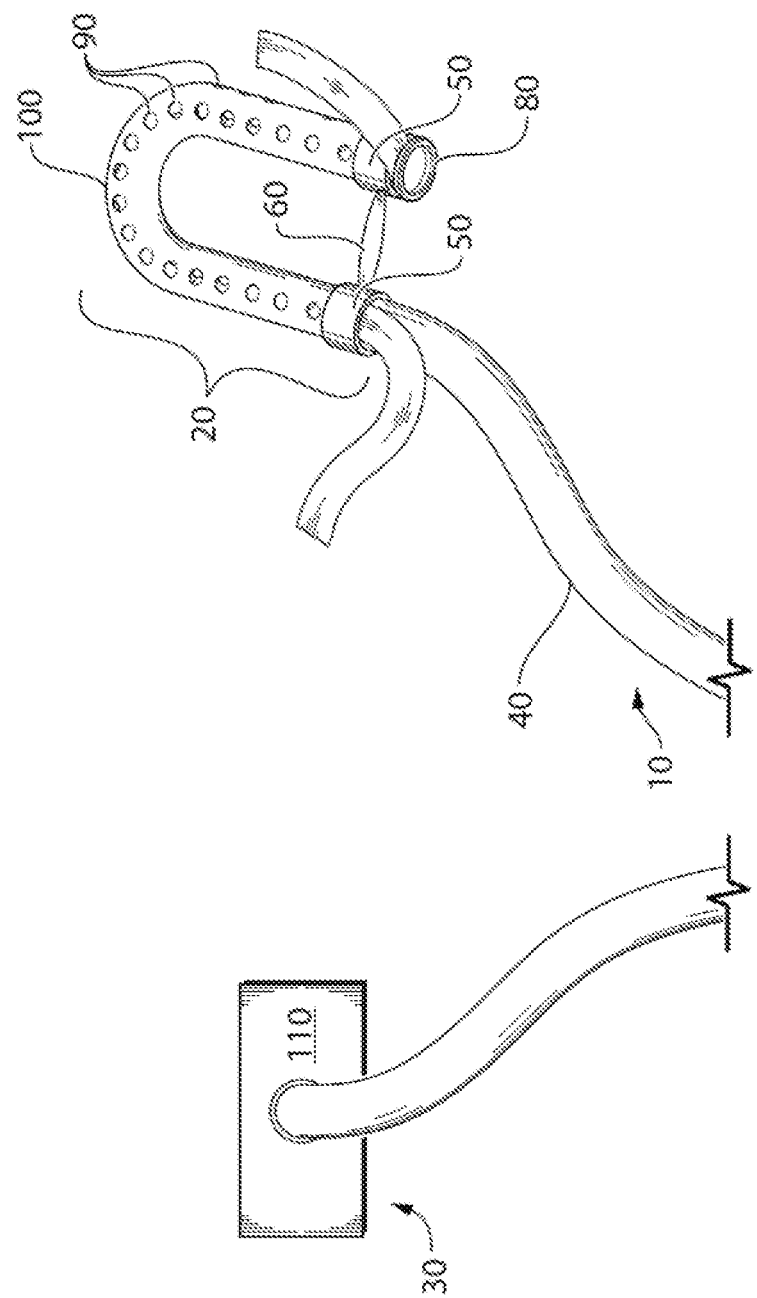
FIG. 1 is a perspective view of a dental suction device having a single tie, according to embodiments of the present disclosure.

The embodiments of the present disclosure generally relate to dental suction devices. In more detail, some embodiments of the present disclosure relate to dental suction devices for capturing aerosols and removal of fluids that are produced and accumulate in a patient's mouth during a dental procedure.

According to some embodiments of the present disclosure, a dental suction device for managing fluid in a patient's mouth comprises a pliable tube or a semi-pliable tube or a bendable tube, each having a first end for connection to a vacuum source and a second end for positioning in a patient's mouth. The second end has a plurality of apertures through which fluid (for example, saliva) or debris is suctioned from the patient's mouth. The dental suction device also comprises one or more pairs of retaining collars. Each of pair of retaining collars comprises a first retaining collar securely positioned a distance apart from a second retaining collar along the second end of the tube. The dental suction device also comprises a tie connecting each pair of retaining collars so as to create a loop at the second end of the tube. The loop is hookable around the terminal end of a row of teeth and each tie is securable between teeth in the row to secure the device in the patient's mouth.

The pliable or semi-pliable or bendable tubing may be formed to accommodate the shape of the patient's mouth. The pliable or semi-pliable or bendable tubing is smooth and flexible thereby minimizing the risk of causing abrasion or bruising to the patient when positioned in the patient's mouth. Furthermore, because the suction device, according to embodiments of the present disclosure, does not require bulky parts or attachments, the device is conducive to patient comfort.

Further, the pliable or semi-pliable or bendable tubing is configured to be looped at the suctioning end thereof for adjustably securing around the terminal end of a row of teeth in the patient's mouth. In this way, the dental suction device may be maintained and operated in the patient's mouth during a dental procedure. Fluid levels in the patient's mouth may therefore be managed without interrupting the dental professional's flow of work.

In order to provide a dental suction device for managing fluid in a patient's mouth and capturing aerosols released during a dental procedure, the above-described dental suction device may be modified to further comprise a housing tube having a first end and a second end, the first end being connectable to the vacuum source, and a funnel that is demountably engaged to the second end of the housing tube. The funnel component of the device may be circular, rectangular, triangular, or any geometrical shape, or any asymmetrical shape such as, for example, a flat or rectilinear side and a circular shape connected to the rectilinear side. The pliable or semi-pliable or bendable tube extends throughout the housing tube and a sufficient length out from the funnel end to allow positioning of the tube around a plurality of teeth at an end of a row of teeth, and securing thereto.

The housing tube and funnel are capable of providing high-volume evacuation (HVE) to a patient's mouth in order to capture aerosols released during a dental procedure. Thus, the housing tube and funnel may be used to provide an HVE system for capturing aerosols while the pliable or semi-pliable or bendable tube, the one or more pairs of retaining collars, and the tie(s) simultaneously act to manage fluids accumulating in a patient's mouth during a dental procedure.

The dental suction devices of the present disclosure may provide a number of advantages. For example, the dental suction device may be easily secured in place by securing the pliable or semi-pliable or bendable tube in place around a row of teeth with a tie between two teeth. This allows the dental suction devices of the present disclosure to be operable in a hands-free manner. That is, the dental professional does not have to manually insert the dental suction device when saliva accumulates in a patient's mouth, or manually reposition an HVE if the patient moves, or if the dental professional's hands obstruct the vacuum provided by the HVE.

Further, because the dental suction devices of the present disclosure are securable inside a patient's mouth, the dental suction devices maintain the shortest possible distance to the source of aerosols, which, in turn, allows a greater percentage of aerosols to be captured as compared to, for example, conventional externally mounted HVEs. As well, due to the proximity of the dental suction devices of present disclosure to a patient's mouth, the dental suction devices may not be affected by a patient's inhaling and exhaling. In contrast, conventional externally mounted HVEs are often affected by a patient's breathing because of their distance from the patient's mouth. For example, a patient's exhaling may have a greater effect on the direction of the flow of an aerosol than the conventional HVE due to the distance of the HVE from the source of the aerosol.

Definitions

Unless defined otherwise, all technical and scientific terms used herein have the same meaning as commonly understood by one of ordinary skill in the art to which this invention belongs.

As used herein, the term "disposable" describes articles that are not intended to be restored or reused and which are intended to be discarded after a single use.

As used herein, the term "rate of fluid removal" refers to the rate at which saliva is being suctioned from a patient's mouth.

As used herein, the term "about" refers to an approximately +/−10% variation from a given value. It is to be understood that such a variation is always included in any given value provided herein, whether or not it is specifically referred to.

Embodiments of the present disclosure will now be described by reference to FIGS. 1 to 19, wherein FIGS. 1 to 6 show embodiments of dental suction devices for managing fluids accumulating in a patient's mouth during a dental procedure, and FIGS. 7 to 19 show embodiments of dental suction devices for capturing aerosols and managing fluid accumulations in a patient's mouth produced during a dental procedure.

Figure 2:
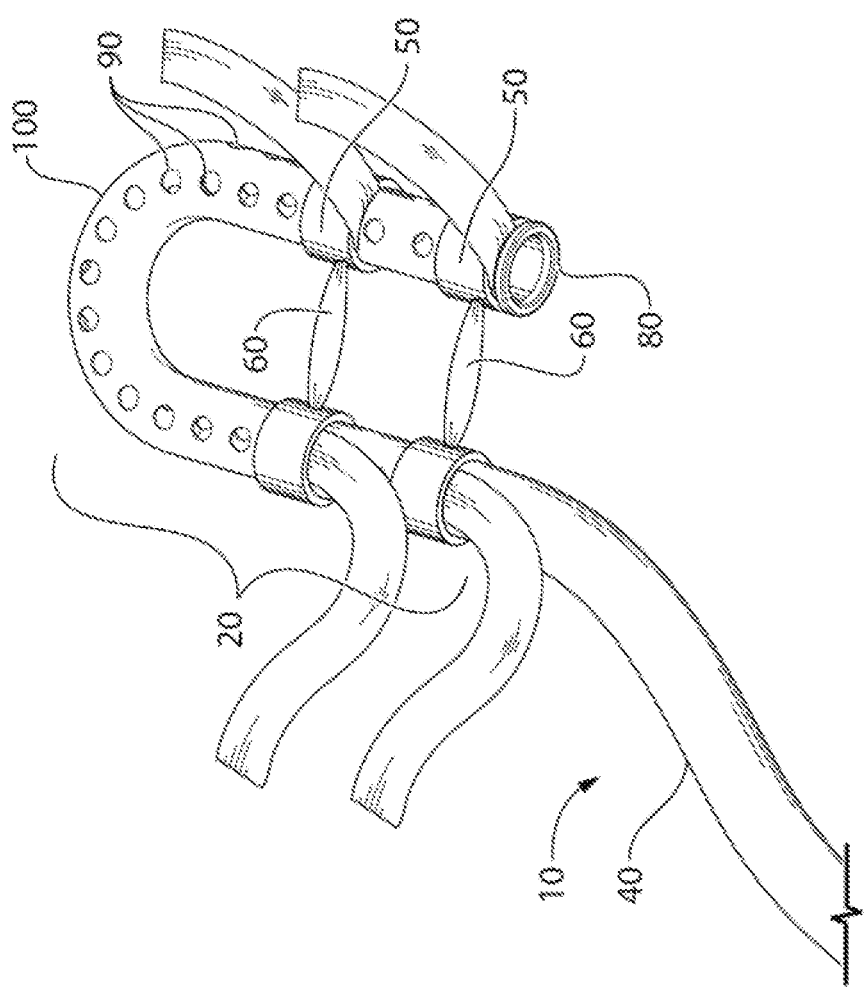
FIG. 2 is a perspective view of a dental suction device having a dual tie, according to embodiments of the present disclosure.

Referring to FIGS. 1 and 2, a dental suction device 10 of the present disclosure comprises a pliable or semi-pliable or bendable tube 40 adapted at a first end 30 for connection to a vacuum source 110 by any suitable connector known to those skilled in the art. The dental suction device 10 may be adapted for connection to any vacuum system appropriate for use in dental practice. The second end 20 of the tube 40 operates as the suction end and is for positioning in a patient's mouth. The second end 20, or suction end, comprises a plurality of apertures 90 through which fluid and debris particles are suctioned from the patient's mouth.

The tube 40 may be made of a semi-rigid polymer including, for example, any suitable plastic, polypropylene, PVC, or polystyrene. Alternatively, the tube 40 may be formed from a waxed paper or a compostable material. The tube 40 may be sufficiently rigid to hold its shape yet pliable enough to bend to form the suction end as will be described below. The size of the tube 40 may be dependent on the application. For human patients, the tube 40 may have an internal diameter of from about 2 mm to about 10 mm. According to certain embodiments, the dental suction device 10 may be adapted for veterinary applications and, in such embodiments, a larger sized tube 40 may be used. For example, according to such embodiments, the tube 40 may have an internal diameter of greater than about 10 mm. According to further embodiments, the tube 40 may have an internal diameter of up to about 30 mm.

The apertures 90 as shown in FIGS. 1 and 2, are evenly distributed at the second end 20 of the dental suction device 10 to form the suction end. The apertures 90 may be in a repeating pattern over the entire second end 20, or alternatively can partially cover the second end 20. According to other embodiments, the apertures 90 may be unevenly distributed at the second end 20 of the tube 40 (not shown), so long as sufficient suction may be achieved to create the suction end.

Figure 3A:
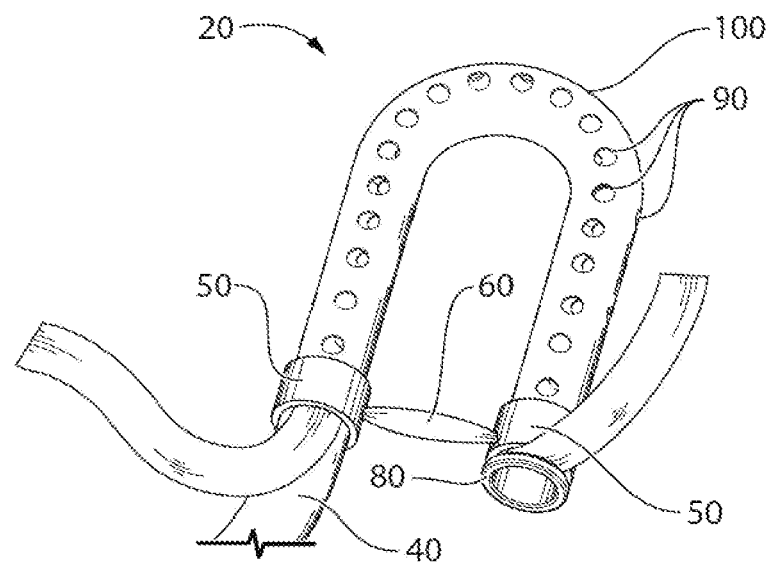
FIG. 3A is a close-up perspective view of the suction end of a dental suction device, according to embodiments of the present disclosure.

As shown in FIG. 3A, the apertures 90 may be circular in shape. According to embodiments of the present disclosure, the circular shaped apertures may range in size and may have a diameter ranging from about 0.25 mm to about 3 mm. According to some embodiments, particularly in applications relating to veterinary dentistry, the diameter of the apertures may exceed 3 mm. According to further embodiment the diameter of the apertures may be up to about 10 mm.

Figure 3B:
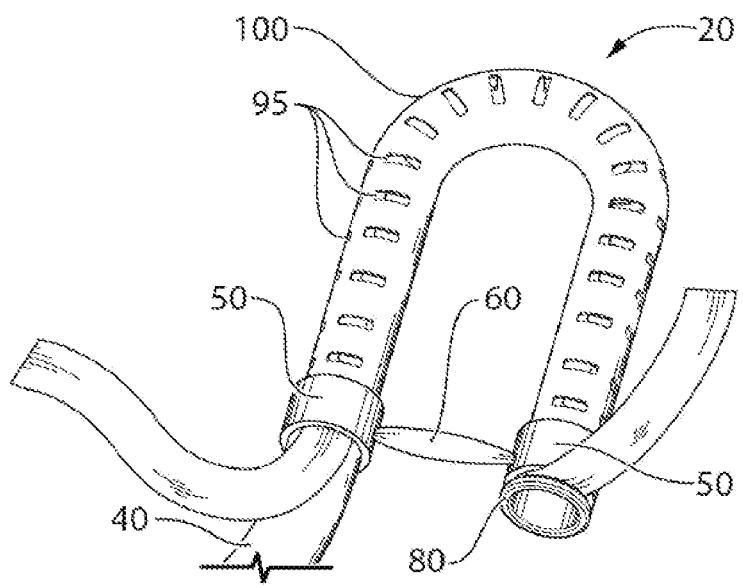
FIG. 3B is a close-up perspective view of the suction end of a dental suction device, according to alternative embodiments of the present disclosure.
Figure 4:
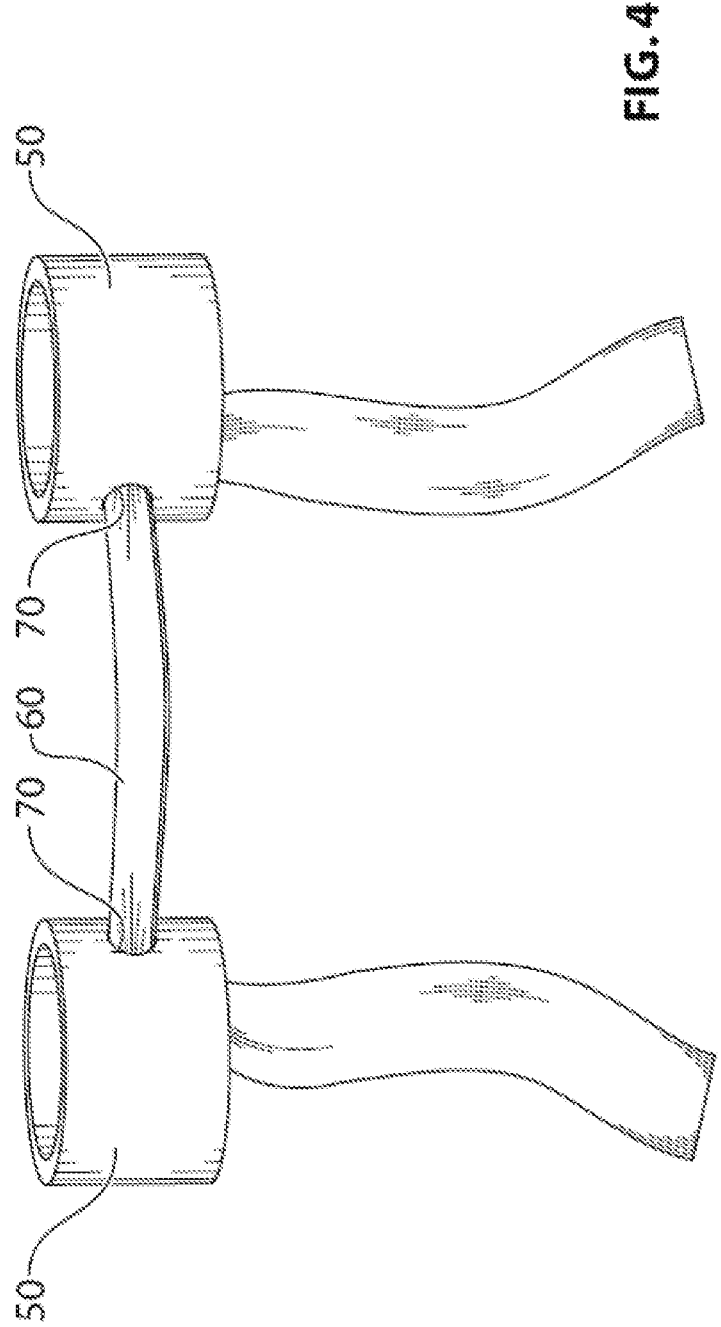
FIG. 4 is a close-up perspective view of a pair of retaining collars and corresponding tie at the suction end of a dental suction device, according to embodiments of the present disclosure.

According to other embodiments, as shown in FIG. 3B, the apertures 95 may comprise a plurality of slits in the tube 40 so long as sufficient suction may be achieved to create the suction end. Persons of skill in the art will appreciate that the apertures may take any shape and size so long as sufficient suction may be achieved to create the suction end.

The second end 20 of the tube 40 may be looped to form the suction end. The length of the second end 20 of the tube 40 must, therefore, be sufficient to allow the second end 20 to form a loop 100. According to certain embodiments, the length of the second end 20 of the tube 40 may range from about 2 cm to about 20 cm, to form a loop 100 of from about 1 cm to about 10 cm, depending on the size of the patient's mouth. According to some embodiments, particularly in applications relating to veterinary dentistry, the length of the second end 20 of the tube 40 may exceed 20 cm, to form a loop 100 exceeding about 10 cm. According to further embodiments, the length of the second end 20 of the tube 40 may be up to about 40 cm, to form a loop 100 of up to about 20 cm.

The loop 100 may be adjusted to any desired size to accommodate a wide range of patients. For example, the loop 100 may be made larger for adults and smaller for children. It is also contemplated that the dental suction device 10 may be used in veterinary dentistry. Accordingly, the loop 100 may further be adjusted to accommodate animals of various sizes. The size and shape of the loop 100 is secured by a pair of retaining collars 50 connected together by a tie 60. Each retaining collar 50 is positioned along the second end 20 of the tube 40 at a certain distance apart from each other. By increasing the distance between the pair of retaining collars 50, the size of the loop 100 may be enlarged. By the same token, by decreasing the distance between the pair of retaining collars 50, the size of the loop 100 may be reduced.

Each retaining collar 50 is sized to fit securely to the outside of the tube 40 in order to maintain the size and shape of the loop 100 forming the suction end, without the risk of slipping during operation. According to some embodiments, the second end 20 of the tube 40 terminates in a flared rim 80 to prevent a retaining collar 50 positioned at the terminal end of the second end 20 from being dislodged off the tube 40. According to certain embodiments, the retaining collars 50 have a diameter large enough to be threadably positioned onto the tube 40 and small enough to be retained by the flared rim 80 at the terminal end of the second end 20 of the tube 40.

According to certain embodiments, the retaining collar 50 and the tube 40 may be made of a semi-rigid polymer including, for example, any suitable plastic, polypropylene, PVC, silicone, and polystyrene. Alternatively, the collar 50 and the tube 40 may be prepared from a waxed paper or a compostable material. In this way, the retaining collar 50 and the tube 40 may have resilient properties and a tackiness in surface tension to further ensure a secure fit. According to certain embodiments, the materials are tolerant to multiple sterilization using methods typically found in dental practice, to allow the dental suction device 10 to be reused. In other embodiments, the dental suction device 10 is for disposable or single use.

Each pair of retaining collars 50 is connected together by a tie 60. When positioned along the tube 40 at the desired distance apart, the pliable tube 40 is bent to connect the pair of retaining collars 50 with the tie 60 and secure the formed loop 100 at the second end 20. According to embodiments of the present disclosure, the tie 60 may be of any suitable material. For example, the tie 60 may be dental floss. According to certain embodiments, the tie 60 may be made of an elastic material. In some embodiments, the elastic material may be latex or non-latex rubber.

The tie 60 is adjustably connected to the pair of retaining collars 50 to allow the loop 100 to be tightened and loosened as needed. According to certain embodiments, and as clearly shown in FIG. 4, each retaining collar 50 in a pair may comprise a hole 70 through which one end of the tie 60 is respectively threaded to allow each end of the tie 60 to be tightly caught between the interior of the respective retaining collar 50 and the exterior of the tube 40. In this way, the tie 60 connects the pair of retaining collars 50 such that pulling a free end of the tie 60 causes shortening of the connection between the respective retaining collars 50 in the pair and tightening of the loop 100. Similarly, releasing the length of the tie 60 between the retaining collars 50 lengthens the connection between the collars 50 causing loosening of the loop 100.

Figure 5:
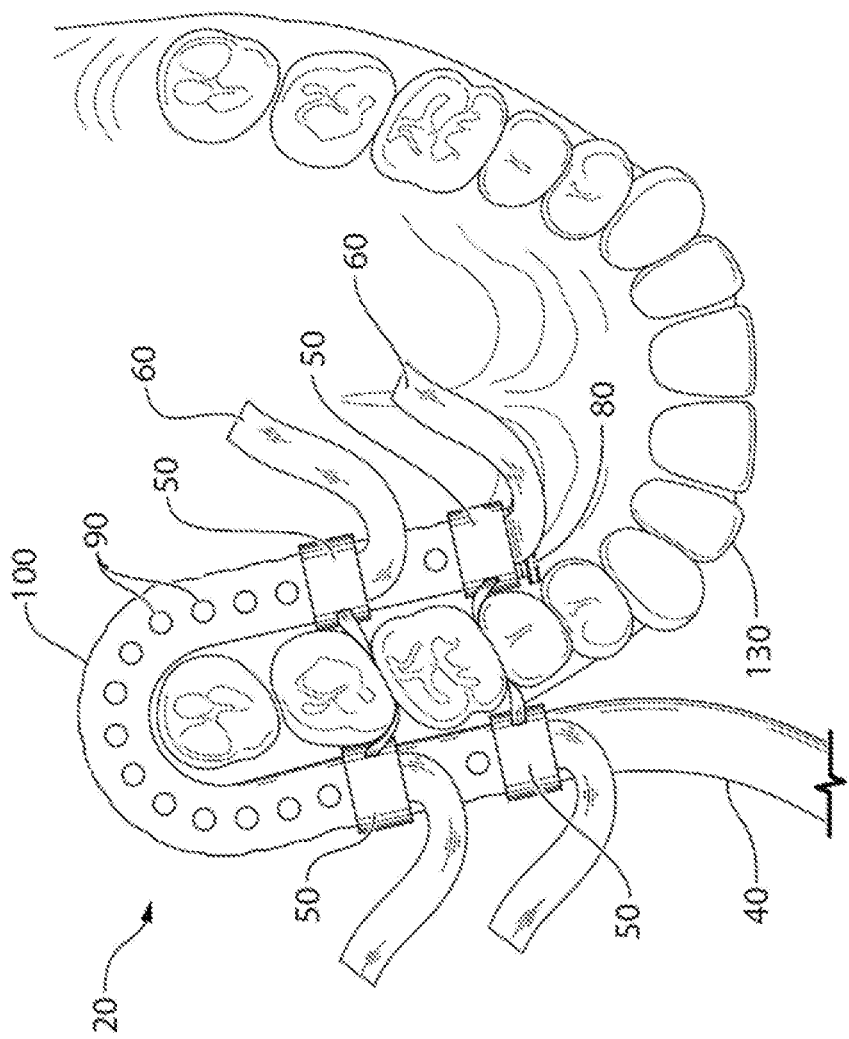
FIG. 5 is a schematic view of a dental suction device, according to embodiments of the present disclosure, positioned in a patient's mouth.

According to embodiments of the present disclosure, as shown in FIG. 5, the loop 100 forming the suction end of the dental suction device 10 may be adjusted to a suitable size and shape to be hooked around the terminal end of a row of the patient's teeth 130. Once positioned, the loop 100 may be tightened by pulling the free end of each tie 60 and then securing the connecting parts of each tie 60 between adjacent teeth in the row 130. In this way, the device 10 is securely positioned in the patient's mouth for removing fluid from the patient's mouth. According to embodiments, the dental suction device 10 is compact and unobtrusive in the tight operating space of a patient's mouth. The dental suction device does not require bulky clamps or fasteners to secure the device in position in the patient's mouth, accordingly, the suction device 10 of the present disclosure may remain in the patient's mouth during a dental procedure without disruption to the dental professional.

The dental suction device 10, as shown in FIG. 5, may be secured to the patient's teeth 130 by two pairs of retaining collars 50 connected between teeth by a respective tie 60. Further embodiments of the dental suction device 10 may include a single pair of retaining collars 50 (FIG. 1), three pairs of retaining collars 50, or more depending on the size of the patient's mouth, the type of dental procedure being carried out, and the location that the vacuum suction is needed in the mouth.

Figure 6:
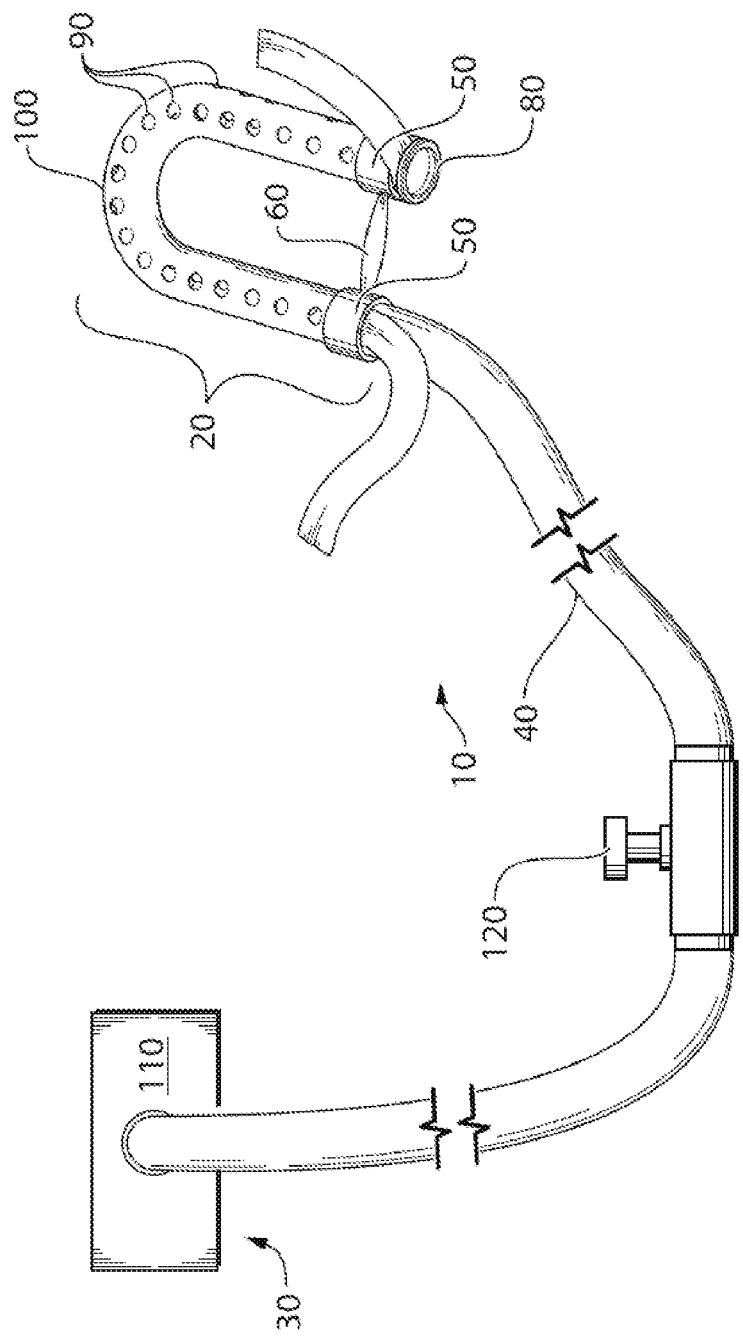
FIG. 6 is a perspective view of a dental suction device adapted for patient control, according to embodiments of the present disclosure.

The dental suction device 10, according to certain embodiments, may be adapted to be directly controlled by the patient during a dental procedure. Referring to FIG. 6, such embodiments may further include a valve 120 located on the tube 40 between the first 30 and second 20 ends. The valve 120 is configured to modulate the rate of fluid removal from the patient's mouth by opening and closing, or partially obstructing, the passageway through the tube 40. In one embodiment, the valve 120 has a plurality of operating positions: in a closed position, no flow passes through the valve 120, in a partially open position, some flow passes through the valve 120 and in an open position, a maximum flow passes through the valve 120. According to certain embodiments, the valve 120 may be movable between the operating positions by a flow control switch that is operable by the patient. According to such embodiments, the valve 120 may be operable by one hand of the patient. The flow control switch is in communication with the valve 120 and enables the patient to control the rate of fluid removal from their mouth during a dental procedure by selecting the desired operating position of the valve 120.

During a dental procedure, the operating positions of the valve 120 may regulate the rate of fluid removal from the patient's mouth. For example, the valve 120 may be set in a partially open position to allow a pre-determined amount of flow to pass through the valve 120. In alternative embodiments, the operating positions of the valve 120 may be continuous between the closed position and the open position so that any amount of flow may be allowed to pass through the valve 120.

In one embodiment, the flow control switch may be a mechanical switch that physically moves the valve 120 between the plurality of operating positions. In one aspect, the mechanical switch is mounted on the tube 40 and applies pressure directly to the tube 40 adjusting the amount of flow through the tube 40. Mechanical flow control switches are well known in the art and therefore will not be described further here. In another embodiment, the flow control switch may be an electrical switch that actuates the valve 120. The electrical switch may include "up" and "down" buttons that actuate the valve 120 between the open and closed positions in increments having a pre-determined size. Electrical flow control switches are well known in the art and therefore will not be described further here.

The simple design of the dental suction device 10 according to embodiments described herein make the device 10 amenable to operate with existing dental vacuum systems. According to certain embodiments, therefore, a system for managing fluid in a patient's mouth during a dental procedure comprises the dental suction device 10 described herein in combination with a vacuum source 110 for supplying a suction vacuum to the dental suction device 10.

To operate the dental suction device 10, according to embodiments of the present disclosure, the suction end formed at the second end 20 of the dental device 10 is placed inside a patient's mouth. Specifically, the loop 100 forming the suction end is secured within the mouth by adjusting the size and shape of the loop 100 to securely hook around the terminal end of a row of the patient's teeth 130. The modular nature of the device 10 further allows the dental professional to adjust the size and shape of the loop 100 to suit the particular patient. For example, pairs of retaining collars 50 may be added or removed as needed to. According to certain embodiments, more than one device 10 may be positioned and operated in a patient's mouth simultaneously. For example, a device 10 may be secured to the terminal end of either or both sides of a patient's upper and/or lower row of teeth 130.

Once the second suction end 20 of the device 10 is secured in the patient's mouth, the first end 30 of the tube 40 extends from the patient's mouth and across the patient's body to connect to the vacuum source 110. According to one embodiment, the vacuum source 110 is turned on during a dental procedure at a suction pressure sufficient to effectively remove fluid from the patient's mouth at a low rate of fluid removal, more specifically at a rate of fluid removal about the salivary flow rate of the patient. Fluid within a patient's mouth flows into the tube 40 through the apertures 90 and is evacuated by standard dental waste practices. In the event an aperture 90 becomes blocked, the plurality of other apertures 90 distributed over the second end 20 may compensate for the blockage and maintain effective operation.

According to certain embodiments, the patient may directly control the rate of fluid removal by manipulating the valve 120. The patient may operate the valve 120 to either increase or decrease the rate of fluid removal as desired according to their comfort. The rate of fluid removal from a patient's mouth is generally at a low rate of fluid removal so that over-drying of the patient's mouth does not occur. More desirably, the rate of fluid removal is about equivalent to the salivary flow rate. Typical salivary flow rates range from between about 0.1 mL/minute and about 0.6 mL/minute, however, a person skilled in the art would understand that salivary flow rates vary between patients.

Referring now to FIGS. 7 to 19, there is shown a dental suction device 200 for capturing aerosols produced and managing fluid accumulations in a patient's mouth during a dental procedure, according to some embodiments of the present disclosure.

Figure 12:
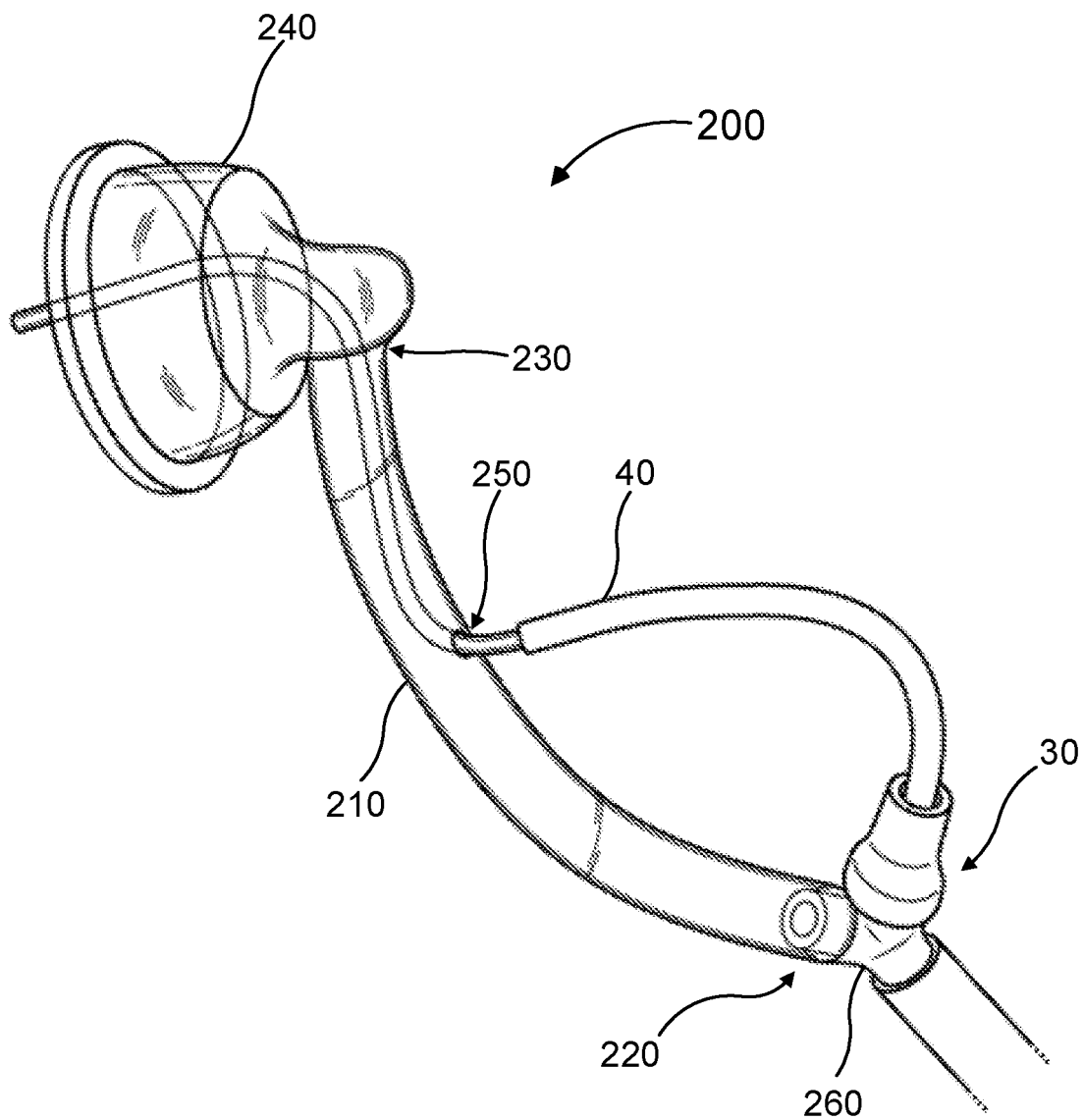
FIG. 12 is a side view of a dental suction device configured for capturing aerosols and removing fluids from a patient's mouth, according to some embodiments of the present disclosure.
Figure 15A:
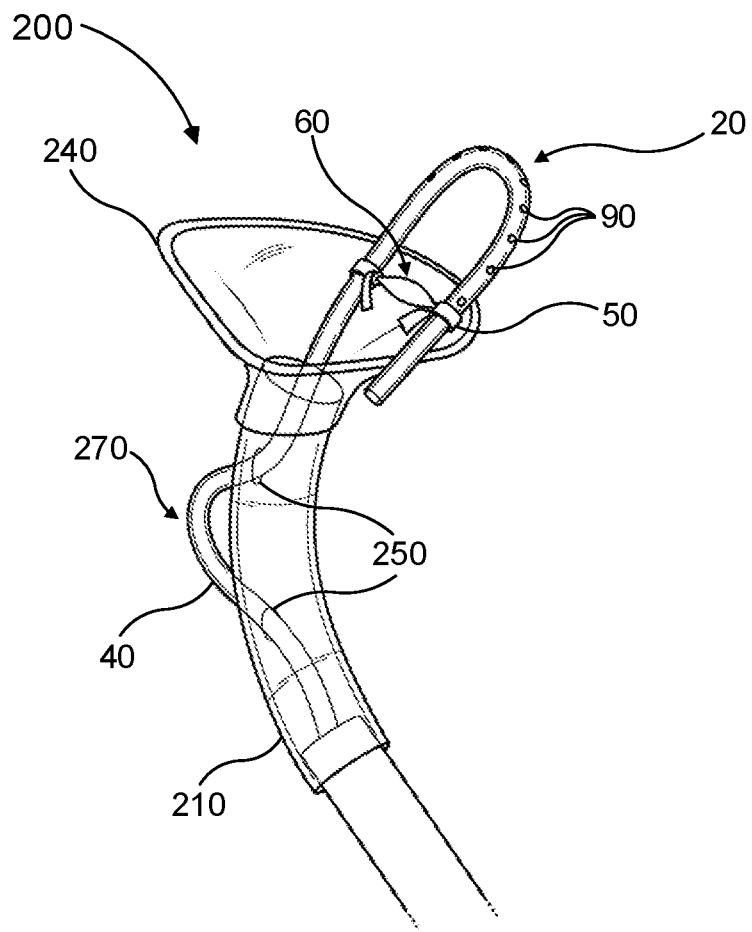
FIG. 15A is a side perspective view of a dental suction device configured for capturing aerosols and removing fluids from a patient's mouth, according to some embodiments of the present disclosure.
Figure 15B:
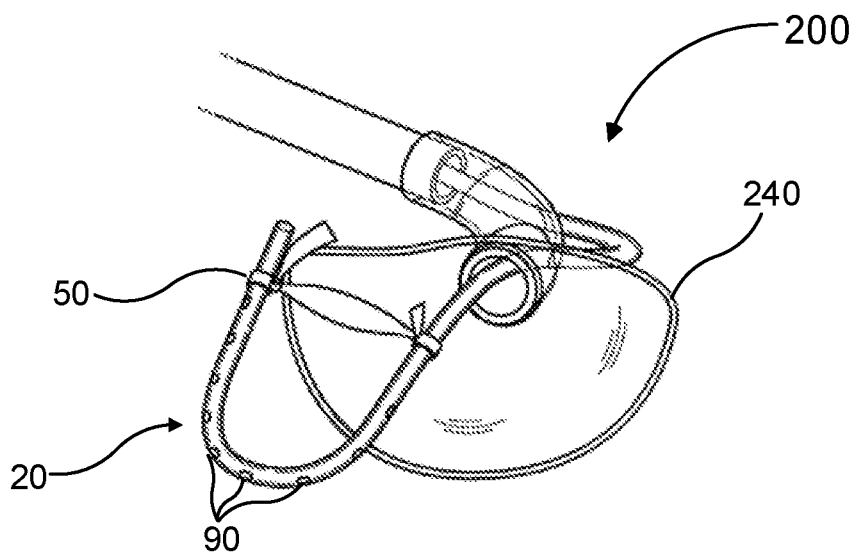
FIG. 15B is a front perspective view of a dental suction device configured for capturing aerosols and removing fluids from a patient's mouth, according to some embodiments of the present disclosure.
Figure 16:
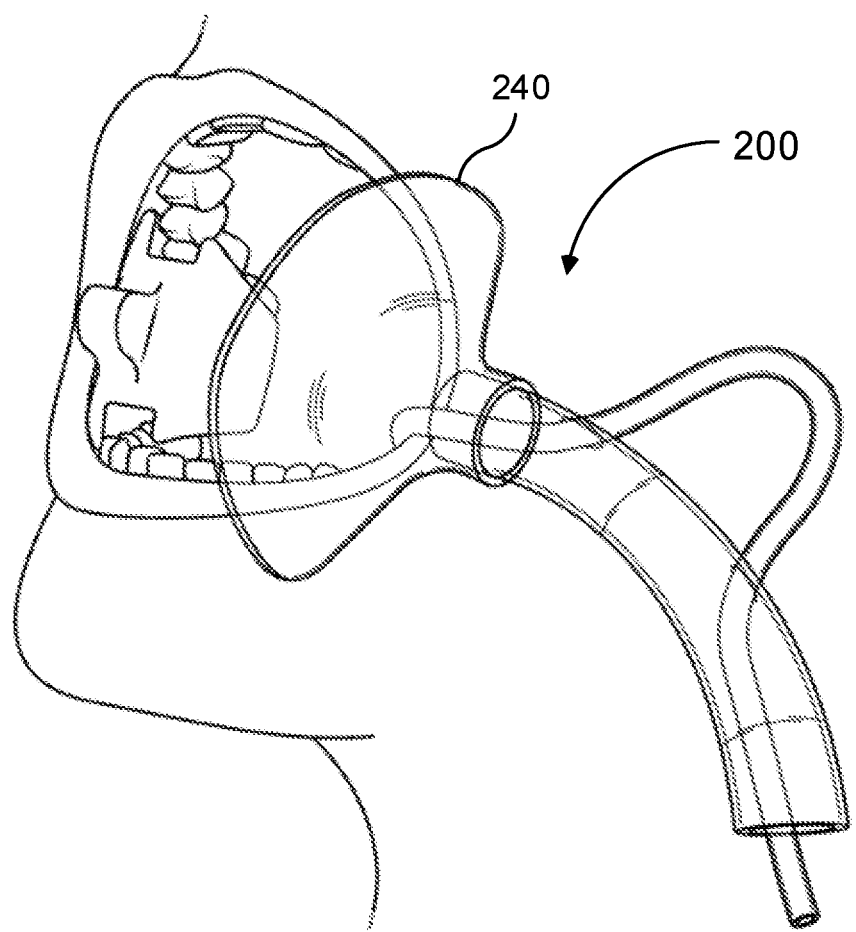
FIG. 16 is a side view of a dental suction device configured for capturing aerosols and removing fluids from a patient's mouth, according to some embodiments of the present disclosure in operation.
Figure 17A:
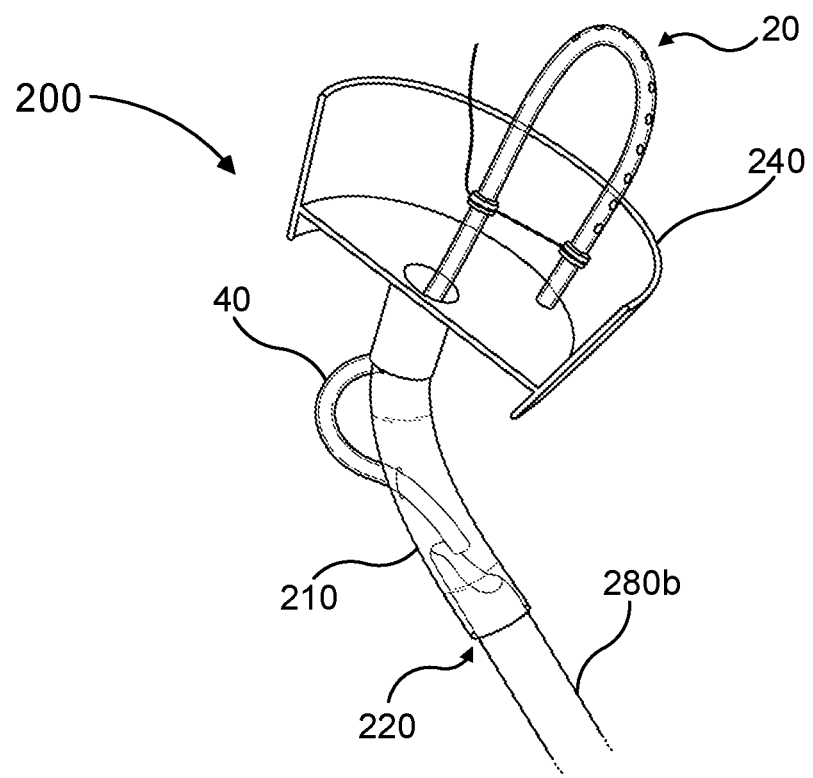
FIG. 17A is a side perspective view of a dental suction device configured for capturing aerosols and removing fluids from a patient's mouth, according to some embodiments of the present disclosure.
Figure 17B:
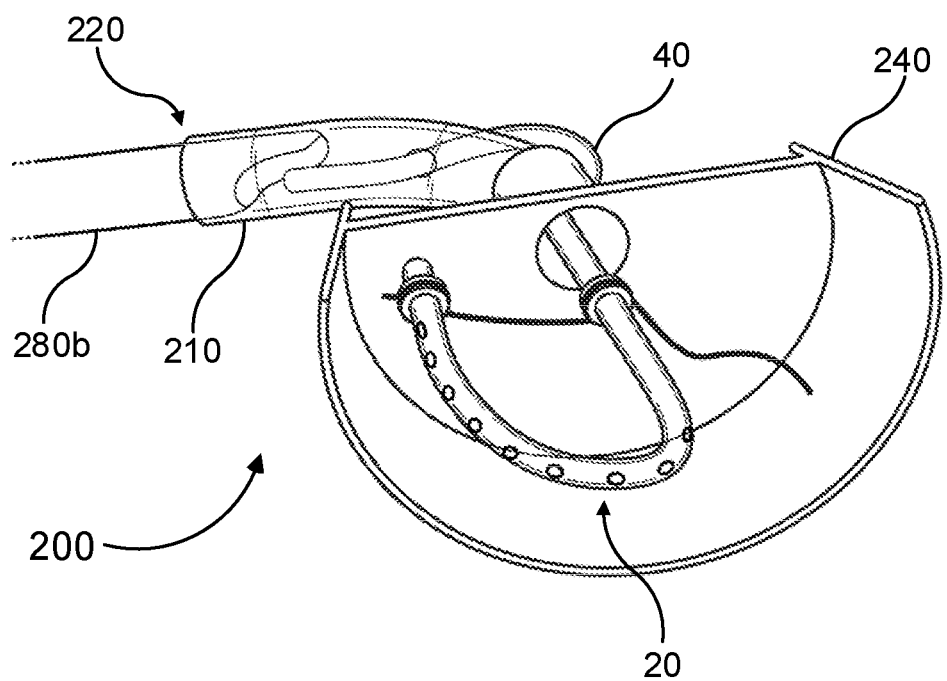
FIG. 17B is a front perspective view of a dental suction device configured for capturing aerosols and removing fluids from a patient's mouth, according to some embodiments of the present disclosure.
Figure 18A:
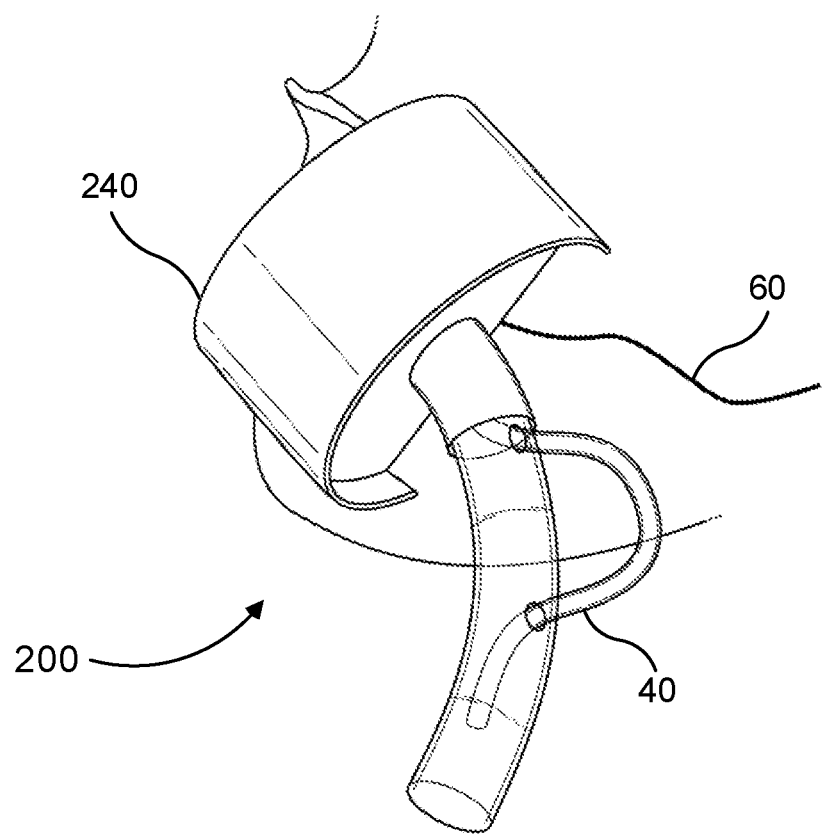
FIG. 18A is a side view of a dental suction device configured for capturing aerosols and removing fluids from a patient's mouth, according to some embodiments of the present disclosure in operation.
Figure 18B:
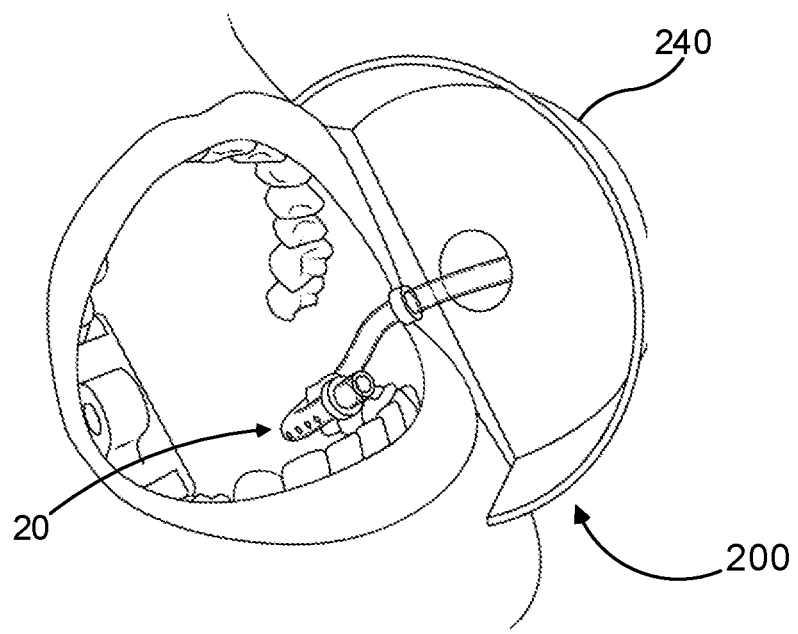
FIG. 18B is a front view of a dental suction device configured for capturing aerosols and removing fluids from a patient's mouth, according to some embodiments of the present disclosure in operation.

The dental suction device 200 comprises a housing tube 210 having a first end 220 that is connectible to the vacuum source 110 and a second end 230. The first end 220 may be connectible to the vacuum source 110 through any suitable means known in the art. As well, it is noted that the connection to the vacuum source may be direct or indirect (for example, by way of another tube, as shown in FIGS. 12, 15A, and 15B). It is also noted that the illustrated housing tube 210 may only be a portion thereof, and the housing tube 210 may be longer than depicted.

According to one aspect, the housing tube 210 may be formed from any suitable materials including, for example, polypropylene, PVC, polystyrene, vinyl, rubber, silicone, and the like. Alternatively, the housing tube 210 may be prepared from a waxed paper or a compostable material. Furthermore, the housing tube 210 may have an internal diameter of about 10 mm to about 30 mm.

The dental suction device 200 also comprises a funnel 240 that is demountably engageable to the second end 230 of the housing tube 210. In the context of the present disclosure, the term "funnel" means a component for guiding a solid, liquid, or gas through a small opening. The funnel be circular, rectangular, triangular, or in any geometrical shape, or asymmetrical shape or their combination, for example, such as a flat or rectilinear side and a circular shape connected to the rectilinear side, as illustrated in FIGS. 15A to 18B, wherein the funnel 240 has a generally semi-circular shape. The flat or rectilinear side may provide additional comfort to the patient when the funnel 240 is positioned external to the patient's mouth (see, for example, FIGS. 16, 18A, and 18B).

Figure 7:
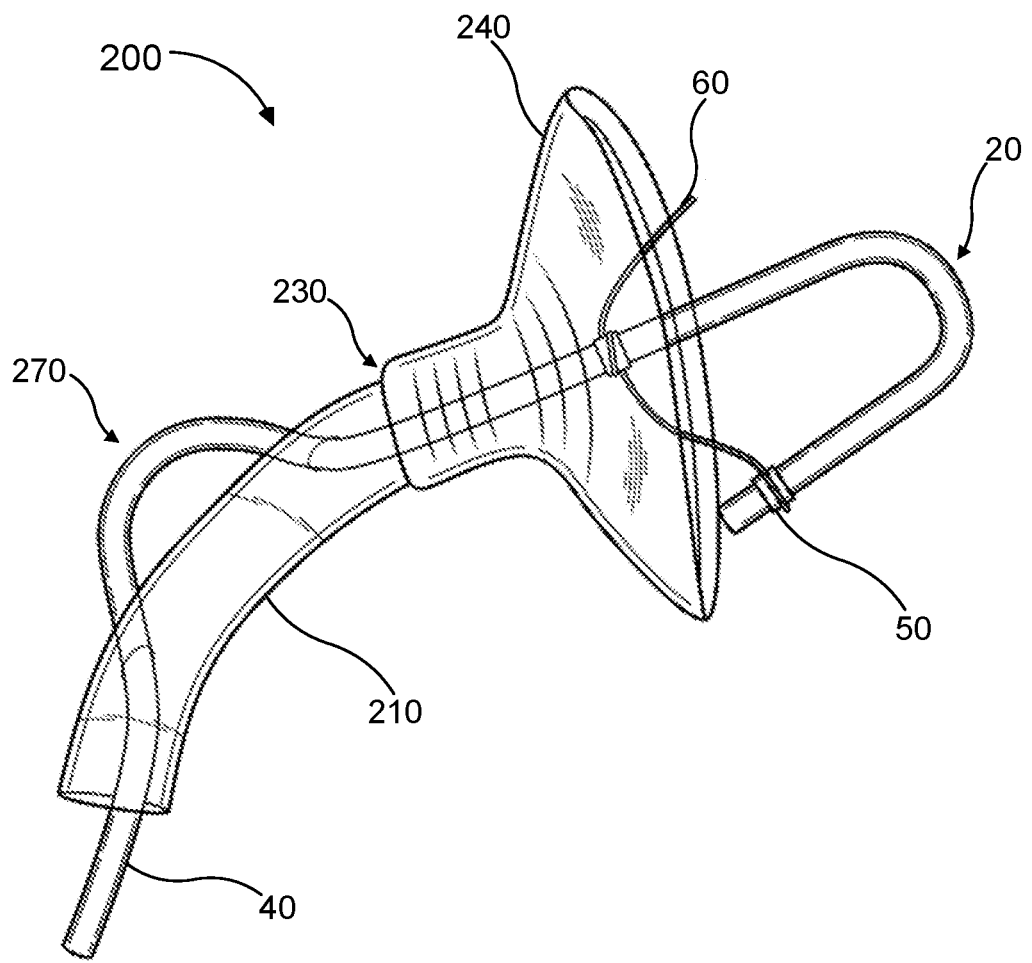
FIG. 7 is a side view of a dental suction device configured for capturing aerosols and removing fluids from a patient's mouth, according to some embodiments of the present disclosure.
Figure 8:
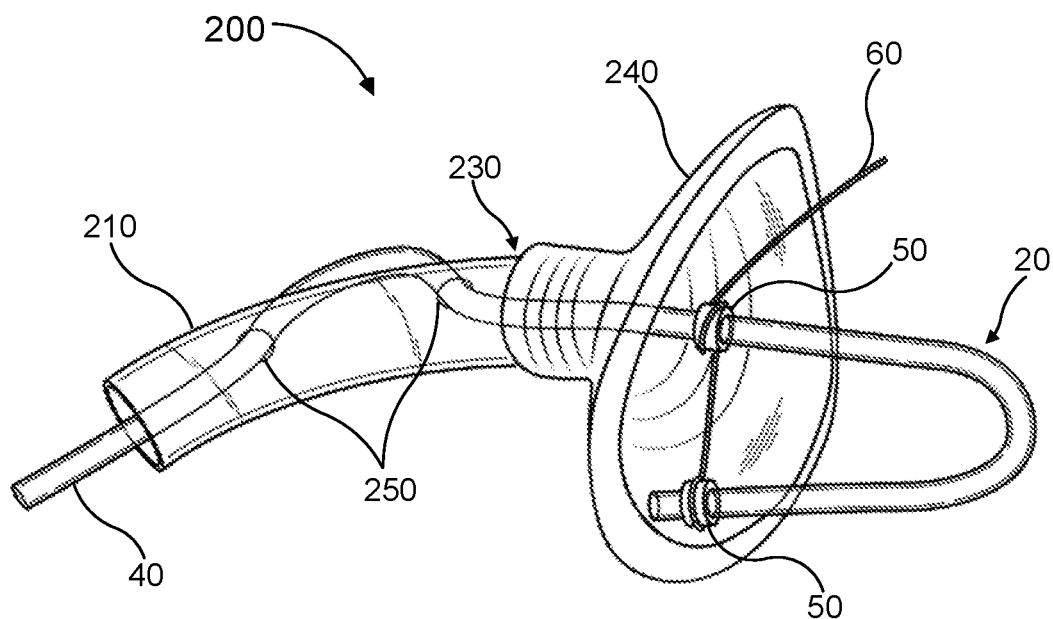
FIG. 8 is a bottom perspective view of the dental suction device illustrated in FIG. 7.
Figure 11:
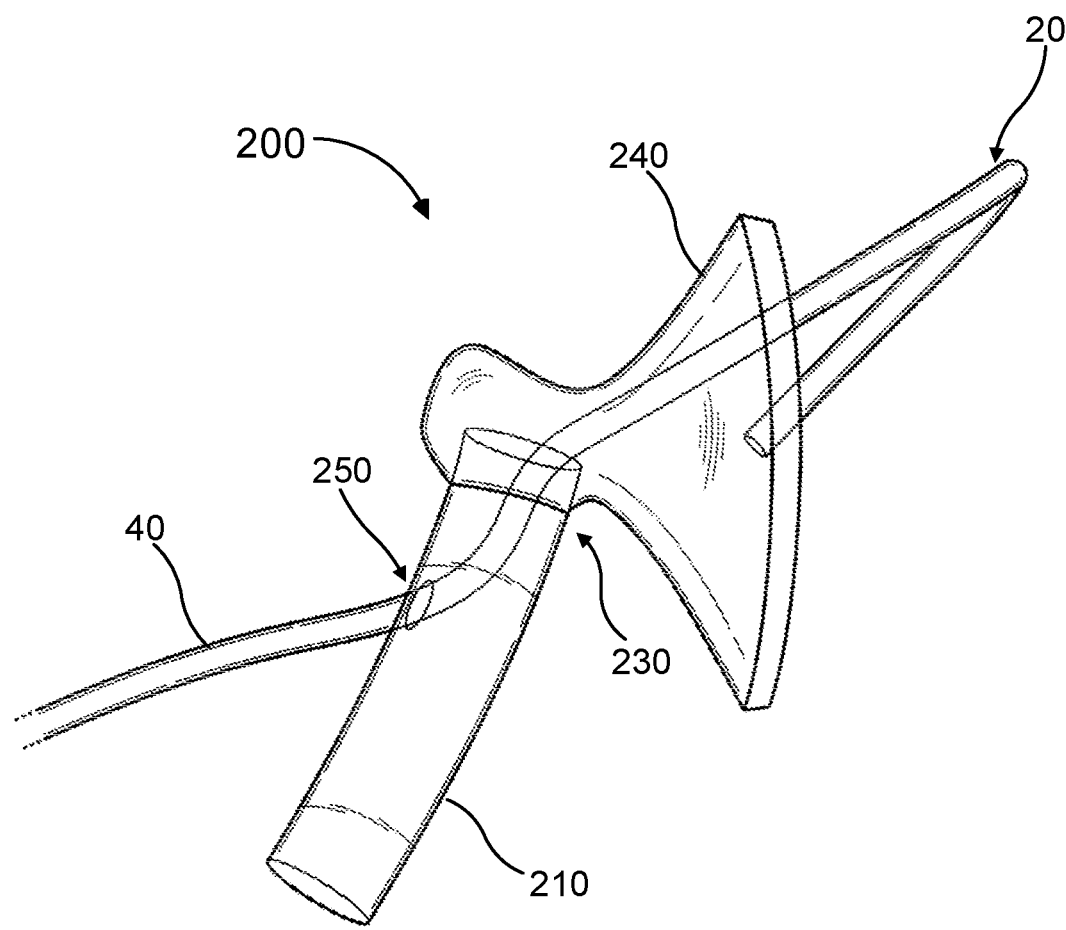
FIG. 11 is a side view of a dental suction device configured for capturing aerosols and removing fluids from a patient's mouth, according to some embodiments of the present disclosure.

The funnel 240 may be connectible to the housing tube 210 by way of, for example, a friction fit, a hose clamp, or the like. In some aspects, the funnel 240 may be configured to receive the housing tube (for example, as in the illustrated embodiment). In other aspects, the housing tube 210 may be configured to receive the funnel 240. Further, in some aspects, the funnel 240 may be connectible coaxially to the housing tube 210, as shown in FIGS. 7 and 8, for example. In other aspects, the funnel 240 may be connectible at an angle to the housing tube 210. As shown in FIGS. 11 and 12, the angle may be about 90° to about 120°. According to some aspects, the funnel 240 and housing tube 210 may be manufactured as a single integrated unit (see, for example, FIG. 19).

The funnel 240 may be formed of any suitable material. In some aspects, the funnel 240 may be formed out of silicone, rubber, polypropylene, PVC, polystyrene, vinyl, or the like. In such aspects, the funnel 240 may be autoclavable for reuse. In other aspects, the funnel may be formed of a compostable material such as a paper material. A compostable funnel 240a is shown in FIGS. 9A, 9B, 17A, 17B, 18A and 18B. In such aspects, the funnel 240a may be disposed after each use.

According to one aspect, the funnel 240 may have a diameter of about 5 cm to about 8 cm at its opening (i.e. the side of the funnel not connectible to the housing tube 210). The portion of the funnel 240 that is connectible to the housing tube 210 may be sized to receive, or be received by, the housing tube 210.

The dental suction device 200 also comprises the pliable or semi-pliable or bendable tube 40 having the first end 30 and second end 20, the at least one pair of retaining collars 50, and the tie 60, each of which may be configured as previously described herein. For the dental suction device 200, the tube 40 extends through at least the funnel 240. In this way, the tube 40 may extend through the funnel 240 such that the second end 20 may be secured in the mouth of a patient by way of the tie 60 and retaining collars 50, as described above, thereby securing the dental suction device 200 in place at or in the patient's mouth, as illustrated in FIGS. 13, 14, 16, 18A, and 18B.

In one aspect, the tube 40 may extend through the center of the funnel 240 (for example, as shown in FIGS. 8 and 9). In other aspects, the tube 40 may extend through an aperture formed in the side of the funnel 240 (not shown). In such aspects, the aperture is sized such that the tube 40 sealingly extends therethrough, that is, the aperture is sized such that gases and liquids may not pass through the aperture when the tube 40 extends therethrough.

Advantageously, the dental suction device 200 may be configured to use a single vacuum source 110 to supply both high-volume evacuation via the housing tube 210 and the funnel 240 to capture aerosols and to manage fluid accumulations in a patient's mouth by way of the tube 40 and second end 20 thereof. For example, tube 40 may extend through the center of the funnel 240 and within the housing tube 210 to the vacuum source 110. Alternatively, the tube 40 may extend at least partially along the housing tube 210 on the outside thereof and connect to the vacuum source 110, for example, via a Y-connector 260 as illustrated in FIG. 12.

Figure 9A:
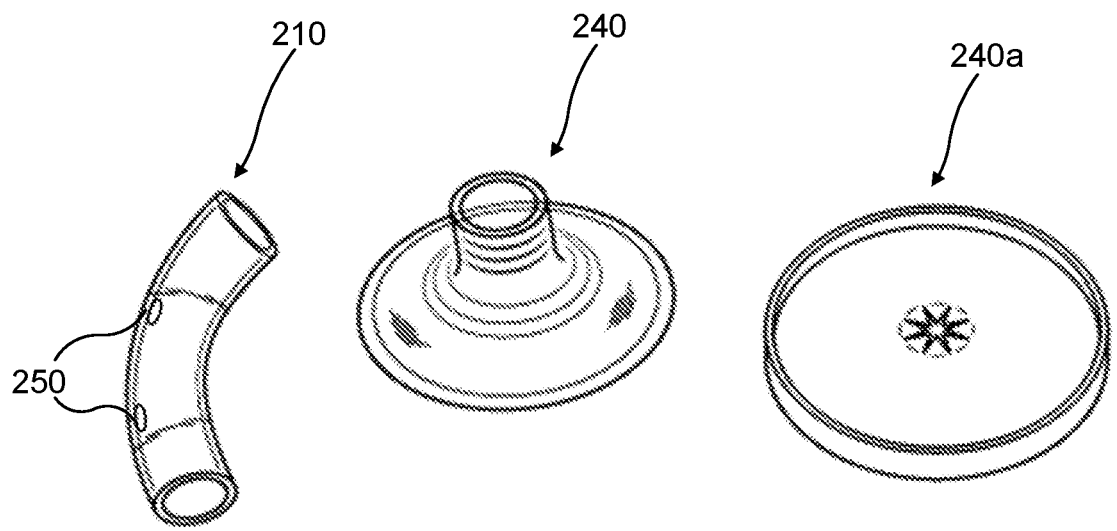
FIG. 9A is a perspective view of components of a dental suction device configured for capturing aerosols and removing fluids from a patient's mouth, according to some embodiments of the present disclosure.
Figure 9B:
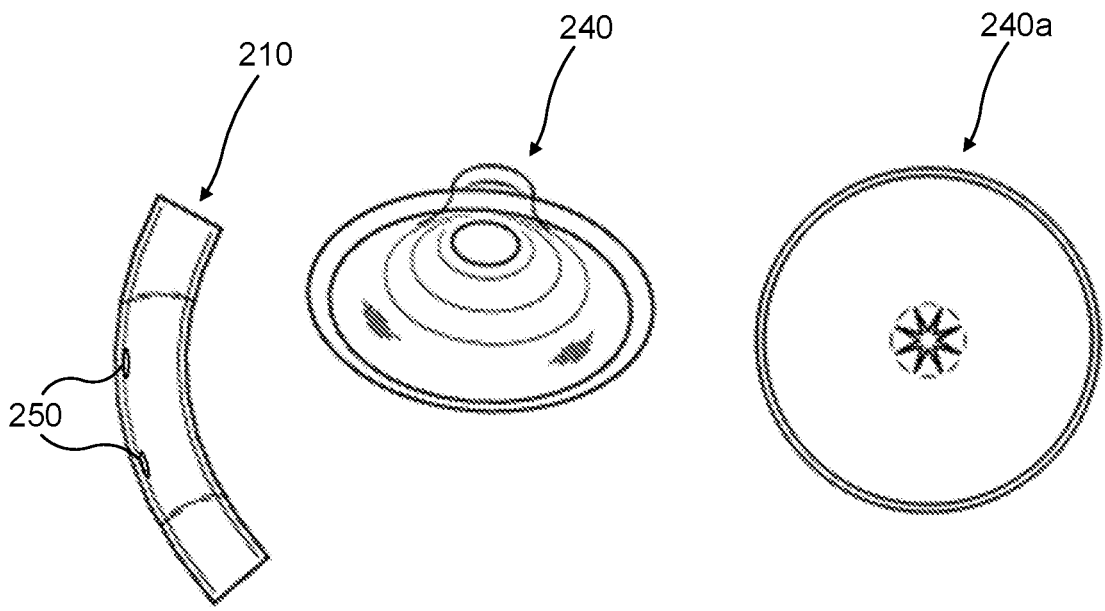
FIG. 9B is another perspective view of components of a dental suction device configured for capturing aerosols and removing fluids from a patient's mouth, according to some embodiments of the present disclosure.

According to one aspect, the housing tube 210 may comprise one or more apertures 250 in a side thereof, as shown in FIGS. 9A and 9B, through which the tube 40 extends. The tube 40 sealingly extends through the one or more apertures 250 in order to secure the tube 40 in place when extending through the center of the funnel 240. This arrangement allows high-volume evacuation to be provided via the housing tube 210 and the funnel 240 at the same time as the suction provided by the tube 40 and second end 20 thereof without the risk of the tube 40 being sucked into the housing tube 210 by the vacuum applied by the vacuum source 110.

In some aspects, the housing tube 210 may comprise two apertures 250. In such aspects, the tube 40 may extend out of the housing tube 210 through a first aperture, back into the housing tube 210 through a second aperture, and through the funnel 240 such that the second end 20 may be secured in the mouth of a patient, thereby securing the dental suction device 200 in place. This arrangement forms a loop 270 with the tube 40 outside of the housing tube 210, as shown in, for example FIG. 7.

Figure 13:
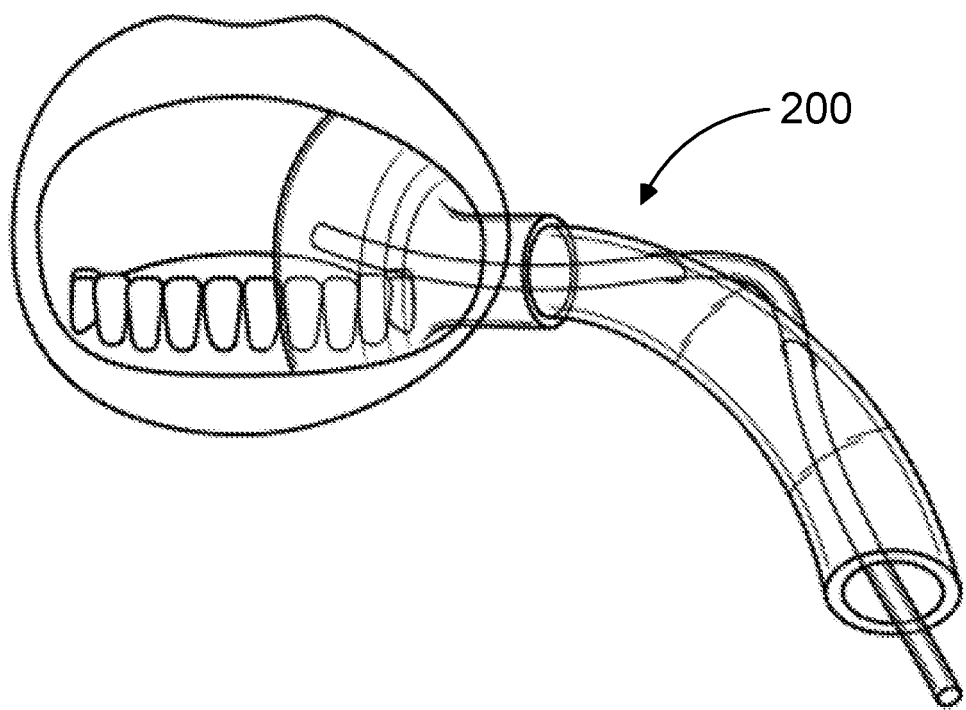
FIG. 13 is a front view of a dental suction device configured for capturing aerosols and removing fluids from a patient's mouth, according to some embodiments of the present disclosure in operation.
Figure 14:
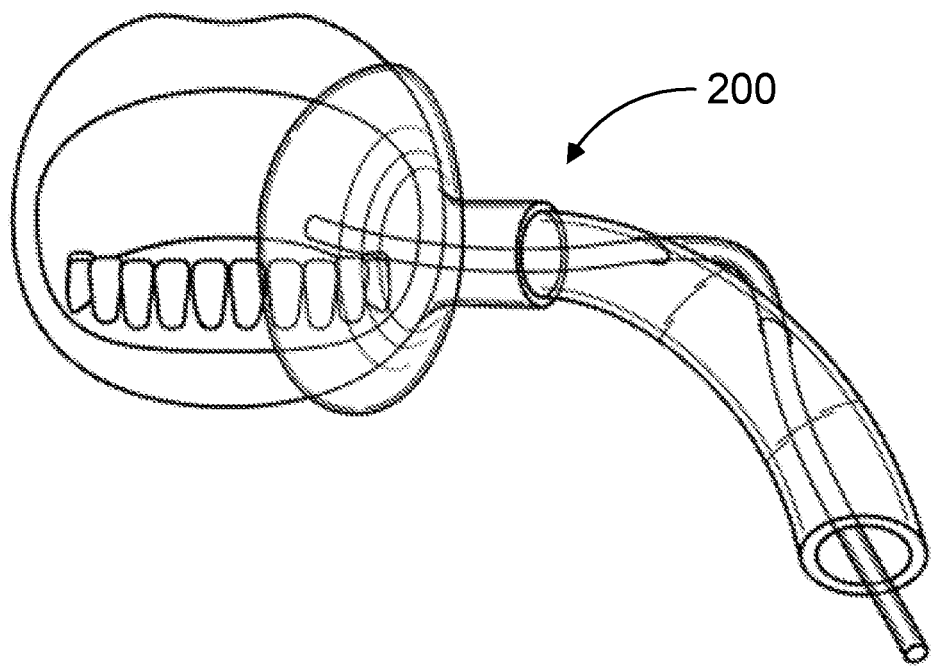
FIG. 14 is a front view of the dental suction device illustrated in FIG. 13 in an alternative operation.

The loop 270 may significantly reduce the risk of the tube 40 being sucked into the housing tube 210 as well as provide an access point to easily adjust the length of the tube 40 extending into the patient's mouth. As a result, the length of the tube 40 extending into the patient's mouth may be manipulated to the position of the dental suction device 200 within or external to the patient's mouth (for example, as shown in FIGS. 13 and 14, respectively).

In other aspects, the housing tube 210 may comprise one aperture 250, as illustrated in FIGS. 11 and 12. The tube 40 may extend through the aperture 250 and through the funnel 240 such that the second end 20 may be secured in the mouth of a patient, to thereby secure the dental suction device 200 in place. In such aspects, the first end 30 may be connected to the vacuum source 110 by way of the Y-connector 260.

In some aspects the housing tube 210 and the pliable tube 40 may be formed integrally together. For example, the housing tube 210 and the tube 40 may be separate ends of a double-lumen tube. In such aspects, the housing tube 210 and tube 40 may be configured as described above (for example, the housing tube 210 may comprise the one or more apertures 250 through which the tube 40 extends). Such aspects may, for example, avoid the need to use the Y-connector 260 to connect both the housing tube 210 and the tube 40 to the vacuum source 110.

Figure 10A:
FIG. 10A is a side view of a muffler according to some embodiments of the present disclosure.
Figure 10B:
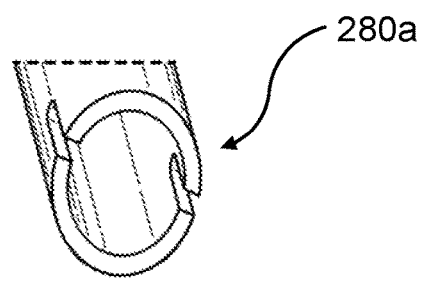
FIG. 10B is a front perspective view of the muffler illustrated in FIG. 10A.
Figure 10C:
FIG. 10C is a side view of a muffler according to some embodiments of the present disclosure.
Figure 10D:
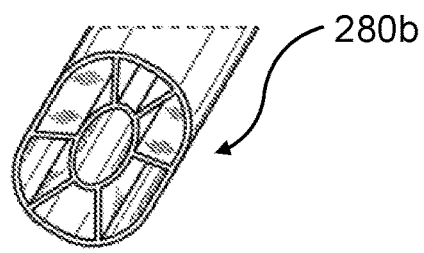
FIG. 10D is a front perspective view of the muffler illustrated in FIG. 10C.

According to a yet further aspect, the suction device 200 may further comprise a muffler 280a or a muffler 280b, as illustrated in FIGS. 10A and 10B and FIGS. 10C and 10D, respectively. The mufflers 280a, 280b may be connected to the housing tube 210 in order to reduce the amount of noise caused by the vacuum source 110 through the housing tube 110 and the funnel 240 when capturing aerosols released from a patient's mouth. FIGS. 10A and 10B show one configuration of muffler 280a having a slotted structure, while FIGS. 10C and 10D show another configuration of muffler 280b having a honey-combed structure. The muffler 280b is shown connected to the housing tube 210 and the tube 40 in FIGS. 17A and 17B.

Figure 19:
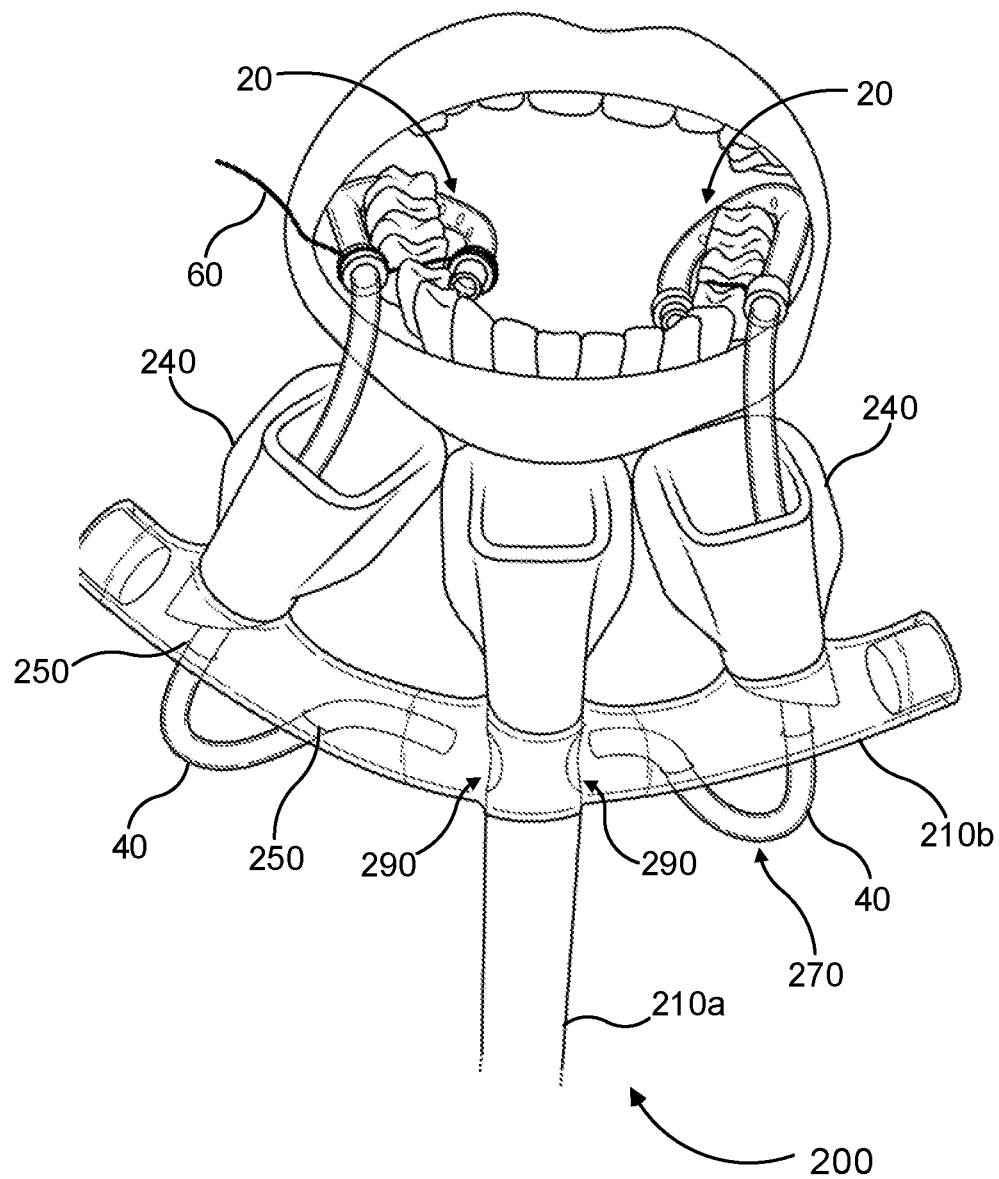
FIG. 19 is a front perspective view of a dental suction device configured for capturing aerosols and removing fluids from a patient's mouth, according to some embodiments of the present disclosure.

According to a yet further aspect, the suction device 200 may comprise a plurality of funnels 240, a plurality of tubes 40, and/or a plurality of housing tubes 210. One such configuration is shown in FIG. 19, wherein the suction device 200 comprises three funnels 240, a first housing tube 210a, a second housing tube 210b, and two tubes 40. In such aspects, the suction device 200 may be secured to a patient's mouth by the tie(s) 60 on each of the plurality of tubes 40, and the plurality of funnels 240 may be positioned in or externally around a patient's mouth.

In more detail, as shown in FIG. 19, the first housing tube 210a engaged with the second housing tube 210b. The second housing tube 210b is connectible to the vacuum source 110 by way of the first housing tube 210a. In the illustrated embodiment, the second housing tube 210b receives the first housing tube 210a in order to engage therewith. The engagement between the first housing tube 210a and the second housing tube 210b may be a demountable engagement or, alternatively, the first housing tube 210a and second housing tube 210b may be manufactured as a single integrated piece.

The first housing tube 210a may be engaged with the second housing tube 210b at a central portion thereof, as in the illustrated embodiment. In such aspects, the second housing tube 210b may comprise an aperture therein for sealingly receiving the first housing tube 210a therethrough for engagement therewith, as shown in FIG. 19. However, the first housing tube 210a may, alternatively, be engaged with the second housing tube 210b at an end thereof, for example, and an aperture for receiving the first housing tube 210a may not be required. It is noted that both the first the first housing tube 210a and the second housing tube 210b may be configured as described above in relation to the housing tube 210 in regards to materials for manufacture and sizing.

The plurality of tubes 40 may extend along through the first housing tube 210a, into the second housing tube 210, and then each through one of the plurality of funnels 240 and into the patient's mouth in order to secure the suction device 200 thereto. In some aspects, the plurality of tubes 40 are separate tubes. In other aspects, the plurality of tubes 40 are separate heads of a double-lumen tube.

In some aspects, such as illustrated in FIG. 19, the first housing tube 210a and one of the plurality of funnels 240 may be manufactured as a single integrated piece. In such aspects, the first housing tube 210a may comprise apertures 290 for each of the plurality of tubes 40 to extend therethrough and into the second housing tube 210b. The apertures 290 are different from the apertures 250 previously described herein in that the tubes 40 do not sealingly extend therethough. Rather, the apertures 290 are wider than the diameter of the tubes 40 so that suction may be delivered to the second housing tube 210b by way of the apertures 290 and the first housing tube 210 while the tubes 40 are present therein.

Further, in some aspects, the second housing tube 210b may comprise a plurality of apertures 250 in one or more sides thereof. As previously described herein the apertures 250 are for sealingly receiving therethrough the tube 40. The second housing tube 210b may have, for example, two apertures 250 per tube 40 for forming the loop 270 with each of the plurality of tubes 40, as described above. The second housing tube 210b in the illustrated embodiment comprises four apertures 250—i.e. two apertures 250 per tube 40.

In the illustrated embodiment, the plurality of funnels 240 comprises three funnels. However, there may be fewer or more funnels 240 engaged therewith (e.g. two, four, etc.). Further, as shown in FIG. 19, the plurality of funnels 240 may be arranged next to and abutting each other, thereby forming an array of the funnels 240. In some aspects, the plurality of funnels 240 may be secured to one another for increased stability. As well, the plurality of funnels 240 may be demountably engaged with the second housing tube 210 or formed as a single integrated unit therewith.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The invention claimed is:

1. A dental suction device comprising:
a housing tube having a first end and a second end, the first end being connectible to a vacuum source;
a funnel demountably engaged with the second end of the housing tube;
a pliable tube or a semi-pliable tube or a bendable tube extending through the funnel, the pliable tube or the semi-pliable tube or the bendable tube having a first end connectable to the vacuum source and a second end for positioning in a patient's mouth, the second end having a plurality of apertures through which fluid is suctioned from the patient's mouth;

one or more pairs of retaining collars, wherein each pair of retaining collars comprises a first retaining collar securely positioned at a distance apart from a second retaining collar along the second end of the pliable tube or the semi-pliable tube or the bendable tube; and a tie connecting each pair of retaining collars so as to create a loop at the second end of the pliable tube or the semi-pliable tube or the bendable tube, wherein the loop is hookable around the terminal end of a row of teeth and each tie is securable between teeth in the row to secure the device in the patient's mouth.

2. The dental suction device of claim 1, wherein the housing tube comprises at least one aperture in a side thereof through which the pliable tube or the semi-pliable tube or the bendable tube extends.

3. The dental suction device of claim 2, wherein the first end of the housing tube and the first end of the pliable tube or the semi-pliable tube or the bendable tube are connectible to the vacuum source by way of a Y connector.

4. The dental suction device of claim 1, wherein the housing tube comprises a first aperture and a second aperture in a side thereof, and the pliable tube or the semi-pliable tube or the bendable tube extends out of the housing tube through the first aperture and into the housing tube through the second aperture.

5. The dental suction device of claim 1, wherein the funnel is demountably engaged coaxially with the second end of the housing tube.

6. The dental suction device of claim 1, wherein the funnel is demountably engaged with the second end of the housing tube at an angle of about 90° to about 120°.

7. The dental suction device of claim 1, wherein funnel comprises an aperture formed in a side thereof through which the pliable tube or the semi-pliable tube or the bendable tube extends.

8. The dental suction device of claim 1, wherein the pliable tube or the semi-pliable tube or the bendable tube extends through a center of the funnel.

9. The dental suction device of claim 1, wherein the pliable tube or the semi-pliable tube or the bendable tube is an inner tube and the housing tube in an outer tube of a double-lumen tube.

10. The dental suction device of claim 1, wherein the funnel is formed of a silicone material, a rubber material, a polypropylene material, a PVC material, a polystyrene material, a vinyl material, a silicone material, a paper material, or a compostable material.

11. The dental suction device of claim 9, wherein the funnel is autoclavable.

12. The dental suction device of claim 9, wherein the funnel is disposable.

13. The dental suction device of claim 1, wherein the housing tube is formed of polypropylene, PVC, polystyrene, vinyl, or rubber.

14. The dental suction device of claim 1, further comprising one or more additional funnels to thereby form an array of funnels.

15. The dental suction device of claim 1 or 14, wherein the funnel has a circular shape, a rectangular shape, a triangular shape, or an asymmetrical shape.

16. The dental suction device of claim 14, wherein the housing tube is a first housing tube, and the array of funnels are connectible to the vacuum source by way of a second housing tube, the second housing tube being engaged with the first housing tube.

17. The dental suction device of claim 16, further comprising one or more additional pliable tubes or semi-pliable tubes or bendable tubes, the one or more additional pliable tubes or semi-pliable tubes or bendable tubes each extending through one of the one or more additional funnels.

18. The dental suction device of claim 17, wherein each of the pliable tube or semi-pliable tube or bendable and the one or more additional pliable tubes or semi-pliable tubes or bendable tubes extend through the first housing tube, into the second housing tube, and through one of the funnels of the array of funnels.

19. The dental suction device of claim 17, wherein each of the one or more additional pliable tubes or semi-pliable tubes or bendable tubes comprises an additional one or more pairs of retaining collars and an additional tie connecting each pair of additional retaining collars.

* * * * *